US 6,584,865 B1

(12) United States Patent
Doherty et al.

(10) Patent No.: US 6,584,865 B1
(45) Date of Patent: Jul. 1, 2003

(54) ABSOLUTE REFERENCE AEROSOL SAMPLER

(75) Inventors: Robert W. Doherty, New Park, PA (US); Paul J. DeLuca, Belcamp, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 12 days.

(21) Appl. No.: 09/801,506

(22) Filed: Mar. 8, 2001

(51) Int. Cl.[7] .............................................. G01N 1/24
(52) U.S. Cl. .................................. 73/863.03; 73/863.23
(58) Field of Search ......................... 73/863.03, 863.02, 73/863.23, 863.25, 864.34, 170.07, 170.08, 170.11–170.14

(56) References Cited

U.S. PATENT DOCUMENTS

| | | | | |
|---|---|---|---|---|
| 2,699,679 A | * | 1/1955 | Munger | 73/863.21 |
| 2,982,131 A | * | 5/1961 | Rosinski | 73/863.03 |
| 3,261,199 A | * | 7/1966 | Raynor | 73/863.03 |
| 3,681,973 A | * | 8/1972 | Ludwig | 73/863.22 |
| 3,740,626 A | * | 6/1973 | Knutson | 73/863.02 X |
| 4,159,635 A | * | 7/1979 | Sehmel | 73/863.03 X |
| 4,475,379 A | * | 10/1984 | Jinotti | 73/28.01 |
| 4,509,727 A | * | 4/1985 | Davis et al. | 73/28.01 X |
| 4,576,054 A | * | 3/1986 | Lalin | 73/863.03 |
| 4,722,746 A | * | 2/1988 | Ho et al. | 73/863.21 X |
| 5,317,930 A | * | 6/1994 | Wedding | 73/863.03 |

FOREIGN PATENT DOCUMENTS

| | | | | |
|---|---|---|---|---|
| JP | 60-151539 | * | 8/1985 | 73/147 |
| JP | 62-156538 | * | 7/1987 | 73/863.02 |
| SU | 1154582 | * | 5/1985 | 73/863.02 |
| SU | 1280478 | * | 12/1986 | 73/863.02 |
| SU | 1437773 | * | 11/1988 | 73/863.03 |

* cited by examiner

Primary Examiner—Thomas P. Noland
(74) Attorney, Agent, or Firm—Ulysses John Biffoni (57) ABSTRACT

An absolute reference aerosol sampler system and method based on isokinetic and isoaxial sampling principles wherein the position of a collection inlet for an aerosol sampling head is adjusted relative to the actual wind direction in real time. In addition, flow rate of the air at a collection inlet within the absolute-reference sampler is matched to the real time actual wind speed. These adjustments and controls enable the absolute reference sampler system to obtain particulate samples from the immediate environment without biasing the size distribution in any manner, resulting in a fully unbiased, representative sample.

19 Claims, 5 Drawing Sheets

ABSOLUTE REFERENCE AEROSOL SAMPLER

GOVERNMENT INTEREST

The invention described herein may be manufactured, used and/or licensed by or for the government of the United States of America.

BACKGROUND OF THE INVENTION

1. Field of the Invention

The present invention relates to an aerosol sampler system. More particularly, the aerosol sampler system of the present invention provides an aerosol sampling that does not disturb the environment upstream of the collected sample. Most particularly, the aerosol sampler system collects aerosol samples in an unbiased manner with respect to aerosol particle size.

2. Brief Description of the Related Art

Sample size bias occurs within most commercially available sample collection systems. This is most commonly a result of the competition between air drag and inertial effects on the aerosol particle due to non-uniformities in the airflow at the entrance of the sample collection system. This problem is addressed by assigning a parameter known as aerodynamic equivalent diameter (AED) which equates a given particle to that of a theoretical spherical particle with a specific standard density, i.e., the theoretical spherical particle displays an experimental aerodynamic behavior that is the same as the real given particle. As such, the particle size is equated with the "aerodynamic equivalent diameter," i.e., the size of a unit density sphere having the same settling velocity as the particle in question, of whatever size, shape or density. Simply viewed, as the flow into a collection entrance becomes increasingly restricted, less massive particles are proportionately forced around the entrance, while the particles having a greater mass are more disproportionately forced into the entrance, resulting in sampling errors.

The currently available sampling devices introduce biasing factors into the collected sample, due to various imperfections and limitations in their design. These samplers generally fall into two categories, omni-directional samplers and fixed direction samplers. Omni-directional samplers generally under-sample larger particle sizes (>10 microns), as the larger particles tend to deviate from the air stream direction due to inertial effects when entering the inlet, resulting in impaction on the inner walls of the inlet. Further complicating the collection process is the fact that the magnitude of the loss of large particles is a function of the ambient wind speed. Similarly, fixed directional samplers generally under-sample larger particles when not aligned with the ambient wind direction, or when sampling at an inlet velocity greater than that of the ambient wind speed. The magnitude of these losses is also a function of wind speed. As a result, even when these sampling flaws are apparent for a given experiment, the affect of these flaws on the collected sample remains unknown.

Accordingly, there is a need to provide an improved aerosol sampling system that collects aerosol samples in an unbiased manner with respect to aerosol particle size. The present invention addresses this and other needs.

SUMMARY OF THE INVENTION

The present invention includes an absolute reference sampler system comprising (A) a positioning component comprising a sampling head having a collection inlet, means for determining wind direction wherein the wind direction is determined in real time, means for comparing the position of the collection inlet and the determined wind direction wherein a differential value is created and means for positioning the sampling head reactive to the differential value and operably connected to the sampling head wherein the means for positioning the sampling head rotates the sampling head for isoaxial alignment with the determined wind direction, and (B) an intake component comprising a mass flow controller, means for determining wind speed wherein the wind speed is determined in real time and means for drawing an effective amount of ambient air into the collection inlet for mass flow controller operation wherein the mass flow controller receives an input for the determined wind speed causing the mass flow controller to regulate ambient air flow into the collection inlet to an air speed substantially equivalent to the determined wind speed.

The present invention also includes a method for ambient aerosol sampling comprising the steps of providing an absolute reference sampler system comprising (A) a positioning component comprising a sampling head having a collection inlet, means for determining wind direction wherein the wind direction is determined in real time, means for comparing the position of the collection inlet and the determined wind direction wherein a differential value is created and means for positioning the sampling head reactive to the differential value and operably connected to the sampling head wherein the means for positioning the sampling head rotates the sampling head for isoaxial alignment with the determined wind direction, and (B) an intake component comprising a mass flow controller, means for determining wind speed wherein the wind speed is determined in real time and means for drawing an effective amount of ambient air into the collection inlet for mass flow controller operation wherein the mass flow controller receives an input for the determined wind speed causing the mass flow controller to regulate ambient air flow into the collection inlet to a speed substantially equivalent to the determined wind speed, and drawing an effective amount of ambient air into the collection inlet wherein the differential value relative to the wind direction and sampling head position is calculated causing the means for. positioning the sampling head to rotate the sampling head proportionally to the differential value to a calculated position and wherein the mass flow controller regulates the ambient air flow into the collection inlet to a speed substantially equivalent to the determined wind speed.

The present invention further includes an ambient aerosol sampling product generated by the process comprising the steps of positioning a collection inlet into isoaxial alignment with a determined wind direction in real time and regulating ambient air flow into the collection inlet to a speed substantially equivalent to a determined wind speed in real time wherein an amount of collected aerosol comprises an unbiased environmental sample.

The present invention isoaxially aligns the collection inlet of the aerosol sampling system with the wind direction and draws an isokinetic sample at an inlet speed equivalent to the wind speed, allowing the collection of an unbiased aerosol sample with respect to aerosol particle size.

DETAILED DESCRIPTION OF THE PREFERRED EMBODIMENT

The present invention provides a system and method to collect a representative sample of ambient aerosols from an open environment. The sampler of the present invention is a device used in the field of aerosol science to collect aerosol particles from the surrounding environment. Once the sampler collects a particle sample, the collected particle sample may then be tested to yield qualitative or quantitative information about the environment from which the sample was collected. The sampler does not disturb the environment upstream of the collected sample, points into the wind, i.e., aligns isoaxially with the wind direction, and ingests samples with an inlet speed equivalent, generally equal, to the ambient wind speed, i.e., achieves an isokinetic state with the wind speed. As the sampler attains this criterion, the collected aerosol sample becomes unbiased for differing aerosol particle sizes within the ambient air. The sampler provides a representative sample of the immediate environment by collecting a sample of the ambient aerosols in the surrounding environment without biasing the sample size distribution, i.e., the collected sample is representative of the surrounding environment. Collection of unbiased samples permits an accurate determination of aerosol concentrations, such as aerosol contaminants within the ambient air.

Figure 1:
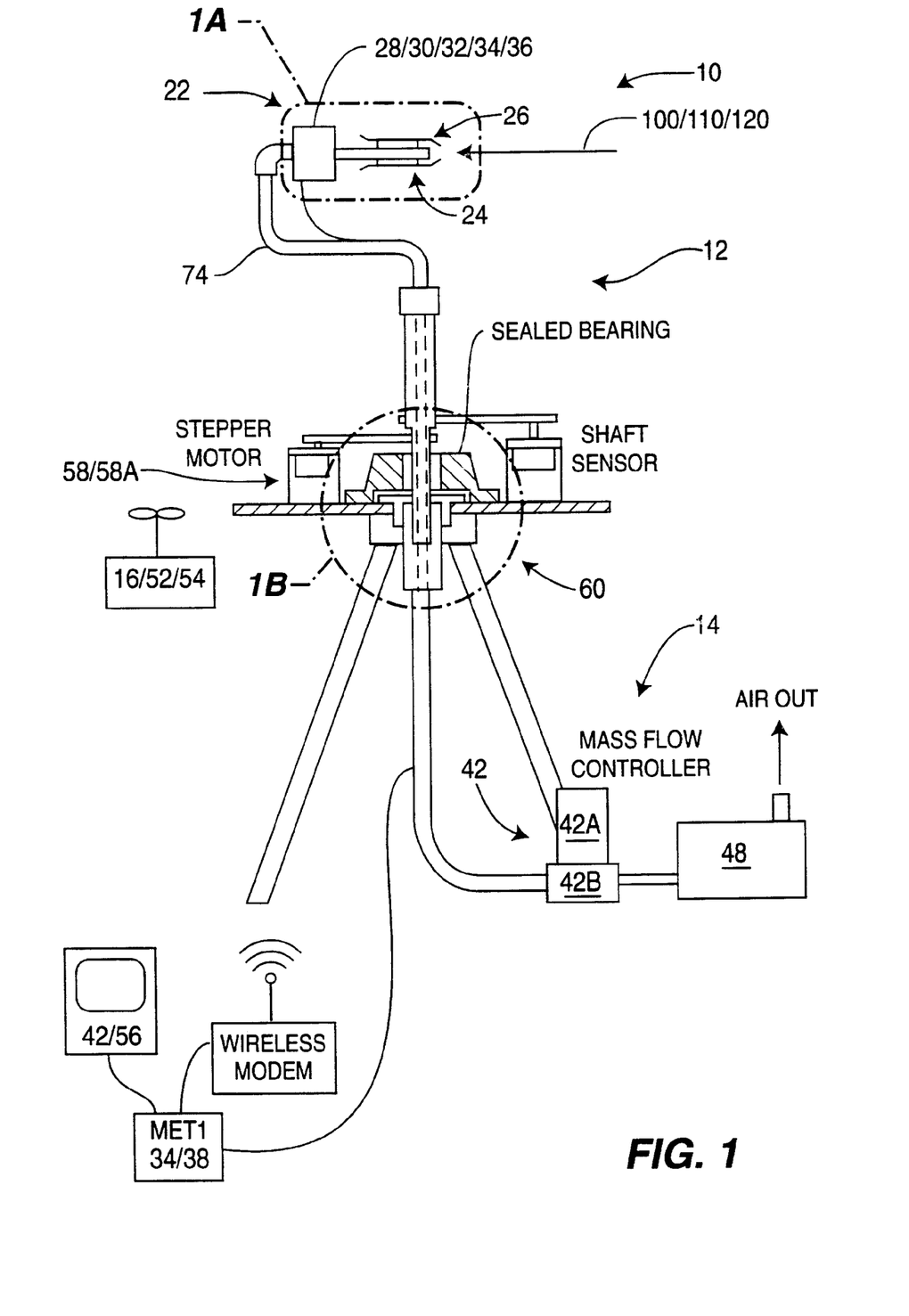
FIG. 1 illustrates the absolute reference sample system of the present invention having a positioning component and intake component, with FIG. 1A illustrating in detail the shroud shown in FIG. 1, FIG. 1B illustrating in detail the airtight sealed bearing system of the absolute reference sample system shown in FIG. 1, and FIG. 1C providing an exploded view of said sealed bearing system.

As seen in FIG. 1, an absolute reference sampler system 10 comprises a positioning component 12 and an intake component 14. The positioning component 12 of the absolute reference sampler system 10 functions to continuously align a sampling head 22 having a collection inlet 24 in substantially isoaxial alignment with a given wind direction 110 as measured within the immediate environment of the absolute reference sampler system 10. The intake component 14 draws ambient air 100 into the collection inlet 24 at a substantially isokinetic rate to a given wind speed 120. Although the position of the sampling head 22 is changed, the sampling head 22 maintains a sealed flow between the collection inlet 24 and a means for drawing 48 an effective amount of ambient air 100 through the use of a sealed bearing system 60.

Figure 1A:
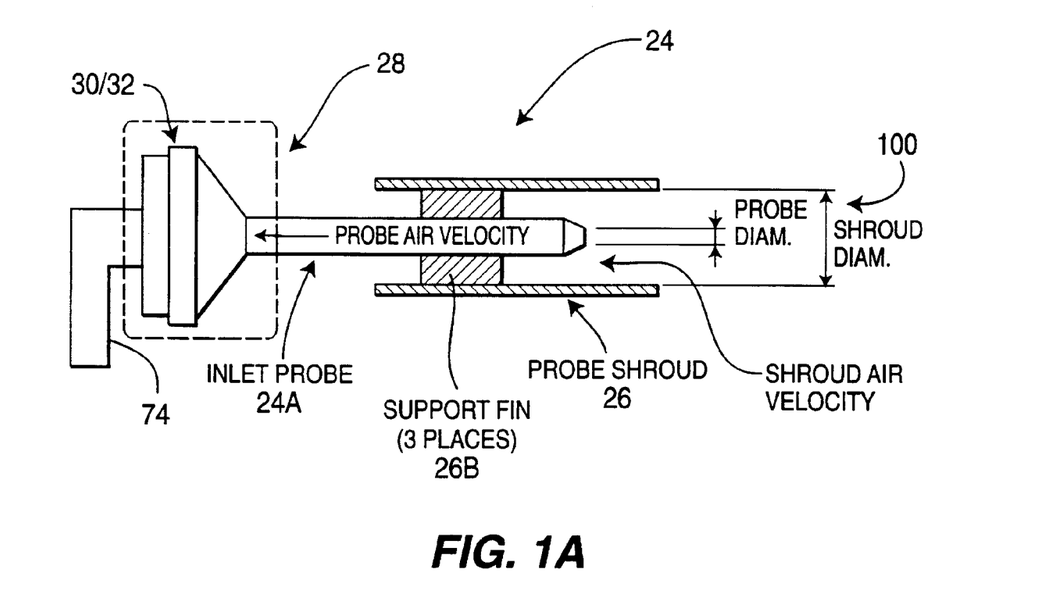
Figure 1B:
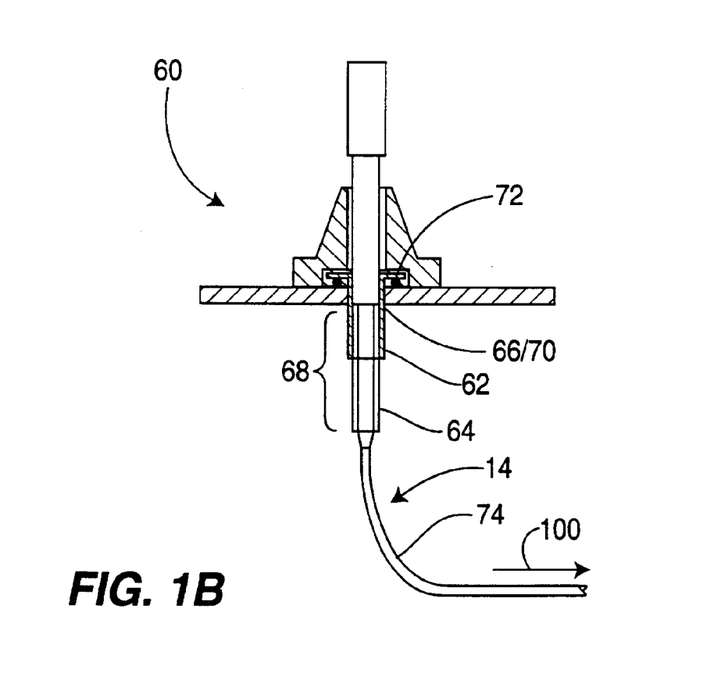
Figure 1C:
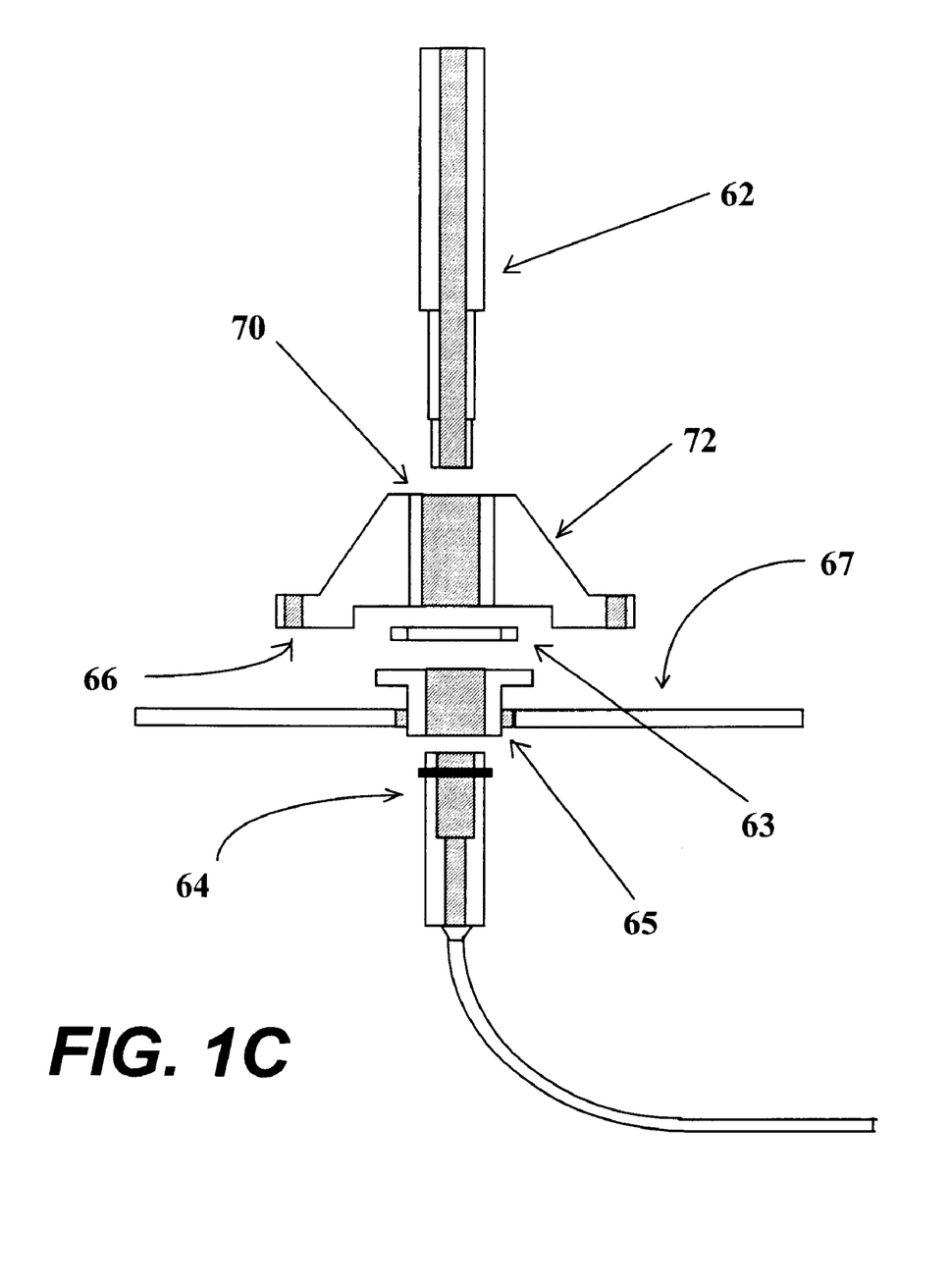

Referring to FIG. 1A, beyond the leading edge or tip of the collection inlet 24, a shroud 26 is preferably used to facilitate the ingress of the air sample into the inlet probe 24A of the collection inlet 24. The shroud 26 includes support fins 26B supporting the outer edges of the shroud 26. Shroud 26 acts to decelerate the incoming ambient air 100. Preferably, the shroud 26 decelerates the ambient air 100 by a factor of from about 2 to about 5, more preferably a factor of from about 3.5 to about 4.5. The proper size and performance characteristics for the shroud 26 for a given absolute reference sampler system 10 are determinable by those skilled in the art, particularly in light of the disclosure of shrouds 26 in the articles "A Predictive Model for Aerosol Transmission through a Shrouded Probe" by Gong et al., Environmental Science & Technology, Vo. 30, No. 11, Pgs. 3192–3198, and "Shrouded Probe Performance: Variable Flow Operation and Effect of Free Stream Turbulence" by Chandra et al., Aerosol Science and Technology, 26:2 February 1997, pgs. 111–126, with the disclosures of these two articles incorporated herein by reference in their entirety. As discussed within these articles, when the shroud 26 is added over the tip of the collection inlet 24, the air entering the collection inlet 24 becomes decelerated by an appropriate factor, as previously described, depending on the geometry of the collection inlet 24 and shroud 26. This deceleration allows the absolute reference sampler system 10 to either utilize less capable mechanisms for drawing air into the collection inlet 24 for the absolute reference sampler system 10 to function in the same range of wind speeds, or to expand the range of wind speeds covered by the same mechanisms for drawing air into the absolute reference sampler system 10, depending on the numerical factor of deceleration provided by the shroud 26. For example, if the shroud 26 decelerates the inlet air velocity by a factor of four, the range of wind speeds measurable by the absolute reference sampler system 10 without the shroud 26 having a range of from 0 to 10 mph advances to isokinetic wind speeds sampling of 0 to 40 mph (4×10) for the absolute reference sampler system 10 with the addition of the shroud 26.

As further seen in FIGS. 1 and 1A, within the sampling head 22, an inspection component 28 is placed along conduit 74 for the collection inlet 24 to collect (retain) or analyze the aerosol particles that entered the collection inlet 24. The inspection component 28 may comprise a collection mechanism, such as a fixed filter holder 30 containing a standard fiber or membrane type filter 32 for collection of the aerosol sample. Once the trial is concluded, the filter 32 is removed from the filter holder 30 and analyzed. Preferably, however, the inspection component 28 comprises a mechanism for immediately analyzing the aerosol sample using an analyzing component 34, such as an optical particle counter/sizer. Exemplary devices include those commercially available as the MET ONE from Pacific Scientific of Grants Pass, Oregon or the TSI Aerodynamic Particle Sizer, with proper mounting and configuration into the sampling head 22 of the absolute reference sampler system 10 determinable by those skilled in the art, such as removing the optical particle detector mechanism to mount it directly to the sampling head 22 while remaining attached electronically through a cable or other means such as a wireless transmitter to the rest of the commercial system, which performs particle counting/sizing functions in a normal manner allowing the user to monitor the data through a dedicated computer 50, shown in FIG. 3. The MET ONE particle counting optics detect the aerosol sample as it passes through a MET ONE optical scanner 36 which is connected to the MET ONE data processing component 38 through a data cable or wireless modem, which then produces size and quantity data on the detected particles.

Preferably, the sampling head 22 comprises a swiveling sampling head 22 that rotates into two directions within a plane above and parallel to the ground, i.e., along the horizontal plane. Within the swiveling sampling head 22, the inspection component 28 is appropriately placed to collect aerosol samples from the drawn ambient air 100. Proper placement of the inspection component 28 is determinable by those skilled in the art in light of the disclosure herein, the main criteria being to avoid turbulence within the collection inlet 24 while creating enough distance from the blunt face of the inspection component 28 to minimize any effect on the particle flow at the inlet tip. Generally, inspection component 28 placement will most appropriately collect or analyze a representative, i.e., unbiased, aerosol sample, such as perpendicular placement directly in the path of the drawn ambient air 100 with the inspection component 28 holding the filter 32 or analyzing component 34 from about 5 inches to about 15 inches from the tip of the collection inlet 24 on the swiveling sampling head 22.

The positioning component 12 moves through a bearing system 60 (detailed in FIG. 1B) located below the positioning component 12. The bearing system 60 of the absolute reference sampler system 10 contains the ambient air 100 flow within the sealed conduit 74 to maintain vacuum for pulling the ambient air 100 through the collection inlet 24. As such, the bearing system 60 seals the conduit 74 between and connecting a means for drawing 48 ambient air 100 and the collection inlet 24. This permits the bearing system 60 to allow efficient rotation of the sampling head 24 while ensuring that only sampled ambient air 100 gets into the intake component 14. The bearing system 60 may include any appropriate mechanism sufficient to accomplish proper functioning of the present invention in light of the teaching herein, with a preferred bearing system 60 comprising a Browning Model FBE920 Flange mounted ball bearing 72 having a one inch (1 in.) diameter shaft 62 press fitted into the bearing hole 70. The shaft 62 protrudes approximately two inches (2 in.) out of the base 66 of the bearing, and mates with a second shaft 64. The interconnection between the bottom of shaft 62 and the top of second shaft 64 is sufficiently aligned and lubricated to form an airtight seal 68 within the tee-shaped collar 65 sitting on support plate 67, while allowing the bearing mounted shaft 62 to swivel inside collar 65, with the second shaft 64 fixed in place within the same collar 65. Both shaft 62 and second shaft 64 have a three-quarters inch (¾ in.) inner diameter through which the ambient air 100 passes as the ambient air 100 is pulled through the conduit 74 by a pump 48. An O-ring seal 63 at the top of shaft 62, underneath the flange mounted ball-bearing 72 and along the outer wall of shaft 64, provides a leak proof seal at these points. The configuration of shaft 62 and second shaft 64 allows the sampling head 22 to rotate while maintaining the conduit 74 sealed for the ambient air 100 to pass, with variations of this design determinable by those skilled in the art in light of the disclosure herein.

Wind direction 110 and wind speed 120 are determined by on-site measurement. Preferably, the absolute reference sampler system 10 includes a portable meteorological station 16 that includes a means for determining wind direction 52 and a means for determining wind speed 54, as well as other devices for measuring and recording environmental conditions such as temperature, true barometric pressure, and relative humidity in the immediate area of the absolute reference sampler system 10. As part of the positioning component 12 of the absolute reference sampler system 10, the means for determining wind direction 52 determines the ambient air 100 wind direction 110 in real time. This provides a reference measurement to maneuver the sampling head 22 in a particular direction to maintain the collection inlet 24 in isoaxial alignment with wind direction 110, which is subject to rapid and repeated changes. Additionally, the means for determining wind speed 54 determines the ambient air 100 wind speed 120 in real time for an additional reference for calibrating a correct ambient air 100 draw into the collection inlet 24. Preferably, both the means for determining wind direction 52 and means for determining wind speed 54 are housed within the meteorological station 16, which may be located in a suitable place for actual wind condition experienced by the absolute reference sampler system 10, with the proper location determinable by those skilled in the art. Preferably, the meteorological station 16 includes several environmental measuring devices for extensive analysis of the collected aerosol sample. While the meteorological station 16 provides real time wind speed 120 and wind direction 110 information for the absolute reference sampler 10 to properly adjust, additional environmental conditions are monitored and/or recorded with these environmental measuring devices in the portable meteorological station 16 such as, without limitation, temperature, barometric pressure and relative humidity. Although preferably portable, the meteorological station 16 may be permanently fixed within a location, as desired, preferably remaining within a three-foot radius of the absolute reference sampler system 10. Portability provides easy relocation of the absolute reference sampler system 10, for either use as a single device in each of several areas and/or use in remote areas. Portable infers a compactness and weight that readily permits transport to and set-up of the absolute reference sampler system 10 in a desired location, such as by transport vehicle or carried by individuals. Preferably, this includes weights of 60 pounds or less, preferably from 30 pounds or less, and sizes not exceeding from about 4 $meters^2$, preferably from about 2 $meters^2$. Real time wind speed 120 data, wind direction 110 and other relevant environment conditions are monitored and recorded using such devices as the ASCII Data Logger 20 and the portable computer 50, which preferably utilize a Metrabyte Data Acquisition or similar card and compatible software such as LabView or LabTech Notebook software for viewing and logging of real time data. Real time determination of the wind direction 110 and wind speed 120 occurs with any appropriate commercially available meteorological system, such as a meteorological sensing device sold under the tradename Anemometer and Meteorological Sensor, Model 500CM-6 manufactured by Cossonay Meteorology Systems of Reading, Pa. for measuring wind speed and direction, temperature, pressure, and relative humidity.

Measurement of real time wind speed 120 permits proper regulation of the ambient air 100 by the intake component 14 into the collection inlet 24. The intake component 14 of the absolute reference sampler system 10 includes a mass flow controller 42 for controlling the intake component 14, i.e., the draw of the ambient air 100 into the absolute reference sampler system 10 and regulating the flow of ambient air 100 into the collection inlet 24. As the means for drawing 48 ambient air 100, such as a pump, draws air into the absolute reference sampler system 10, the mass flow controller 42 ensures ambient air 100 draw remains referenced to the actual wind speed 120 of the ambient air 100 outside of the absolute reference sampler system 10. The mass flow controller 42 preferably comprises a flow meter 42A and a valve 42B for referencing the ambient air 100 draw into the absolute reference sampler system 10. The flow meter 42A component of the mass flow controller 42 measures the amount of ambient air 100 passing through the mass flow controller 42. This measurement of ambient air 100 by the flow meter 42A is used, in real time, to control the valve 42B. The valve 42B of the mass flow controller 42 allows the mass flow controller 42 to vary this amount of ambient air 100 passing through the mass flow controller 42. In combination, the flow meter 42A and valve 42B function to equate the draw of ambient air 100 into the absolute reference sampler system 10 with the external environmental wind speed 120 conditions. Preferably, the two functional parts of the mass flow controller 42, i.e., the flow meter 42A and the flowmeter valve 42B, are integrated into a single unit. The valve 42B preferably comprises a proportioning valve 42B. Selection of a suitable mass flow controller 42 is determinable by those skilled in the art in light of the disclosure herein, for example, a mass flow controller 42 being commercially available under the tradename of Matheson, manufactured by Matheson Gas Products of Montgomeryville, Pa.

In one preferred embodiment, the mass flow controller 42 responds to a command voltage input (determined by the wind speed) ranging from 0 to 5 volts dc. At an input of 0 volts dc, the valve is fully closed, while for an input of 5 volts dc the valve is fully open. All voltages in between 0 and 5 respond in a linear manner, i.e., for an input of 2.5 volts the valve is half opened. For a vacuum pump 48 and mass flow controller 42 with a maximum flow capacity of 50 standard liters per minute (slpm) throughput, an input of 2.5 volts dc would yield a throughput of 25 slpm, an input of 1.25 volts dc yields 12.5 slpm, and other voltages being likewise linearly proportional to the throughput of the valve 42B.

If the collection inlet 24 does not include the shroud 26, the velocity of the air entering the collection inlet is set equal to the ambient wind speed which corresponds to a flow meter 42A reading by the equation I below, where flowrate and wind speed are referenced to standard temperature at 20° C. and standard pressure at 1 atmosphere:

$$\text{Flowrate} = (\pi/4)(\text{Diameter}_{Inlet})^2 \times \text{Wind Speed} \qquad (I)$$

This encompasses the condition of isokinetic inlet sampling in which the wind velocity at the collection inlet 24 equals the ambient air speed 120. When the shroud 26 is placed over the collection inlet 24, with the inlet probe diameter 30% of the shroud diameter, the required system flowrate is reduced by a factor of 4 relative to the unshrouded inlet, and is described by equation II below:

$$\begin{aligned}\text{Flowrate} &= (\pi/4)(\text{Diameter}_{Inlet})^2 \times (\text{Wind Speed})/4 \qquad (II)\\&= (\pi/4)(0.3 \text{Diameter}_{Shroud})^2 \times (\text{Wind Speed})/4\\&= 0.0225\pi(\text{Diameter}_{Shroud})^2 \times (\text{Wind Speed})/4\end{aligned}$$

Accordingly, in the case of a shrouded probe, the inner probe 24A has a flowrate only 0.0225 times the ambient flow 100 entering the shroud 26. This provides a substantially equivalent wind speed at the shrouded probe compared to the actual wind speed conditions to compensate for an isokinetic condition. As such the flowrate of the shrouded probe is shown in equation III below:

$$\text{Flowrate} = x\pi(\text{Diameter}_{Shroud})^2 \times (\text{Wind Speed})/4 \qquad (III)$$

where x is determinable by those skilled in the art for a given shroud configuration and size.

The intake component 14 further includes the means for drawing 48 an effective amount of ambient air 100 into the collection inlet 24. An effective amount includes sufficient ambient air 100 flow for mass flow controller 42 operation to match the speed of the ambient air 100 flow into the collection inlet 24 with the real time determined wind speed 120. The means for drawing 48 includes any suitable vacuum device that functionally draws enough ambient air 100 into the collection inlet 24. Preferably, the means for drawing 48 ambient air 100 into the collection inlet comprises a pump 48. Such devices include, without limitation, mechanical, electrical or pneumatic pumps, with the proper selection of pump or other suitable drawing device determinable by those skilled in the art in light of the disclosure herein. For proper continuous functioning, the selected pump 48 should be capable of pulling against a complete vacuum, i.e., against a closed system, without sustaining damage.

Figure 2:
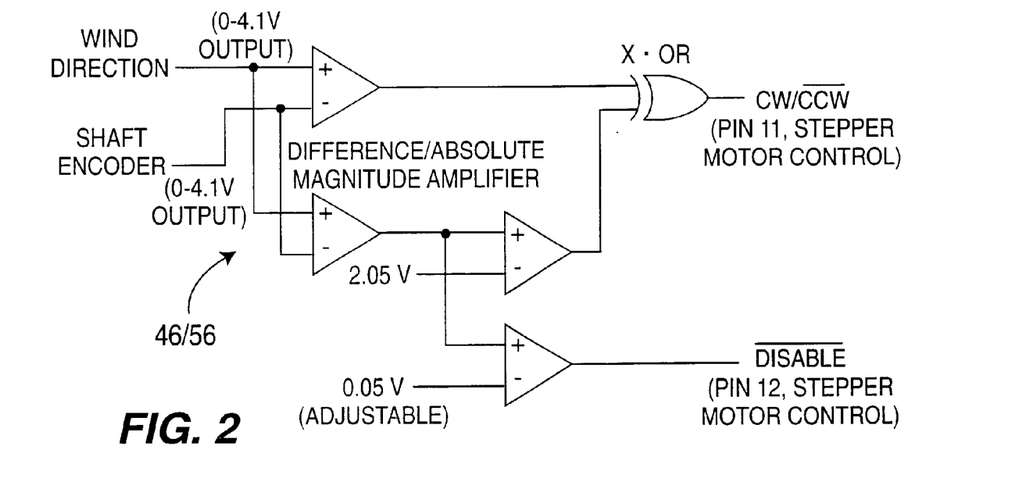
FIG. 2 is a schematic representation of the comparator circuit of the present invention for controlling the positioning component.

FIG. 2 shows a schematic representation of a comparator circuit 46 used by the present invention for controlling the positioning component 12. As seen in FIGS. 1 and 2, the means for comparing the position of the collection inlet 24 and the determined wind direction 110 preferably comprises the comparator circuit 46 for controlling the sampling head 22 position. Wind direction 110 data is used to control a stepper motor feedback system 58A to swivel the sampling head 22 which is achieved through the comparator circuit 46 which compares the output of a position sensor, attached to the shaft of the sampling head 22, with the wind direction 110 data, instructing a stepper motor 58 to turn either clockwise or counter clockwise until the desired position is reached, at which time the stepper motor 58 is disabled until the wind direction 110 changes.

As seen in FIG. 2, the absolute reference sampler system 10 comparator circuit 46 acts as a means for comparing 56 the position of the collection inlet 24 and the determined wind direction 110, to ensure isoaxial alignment of the collection inlet 24 with the actual wind direction 110. Position comparison between the position of the collection inlet 24 and the wind direction 110 yields a differential value that is created to represent any variance between the position of the collection inlet 24 and the determined wind direction 110, i.e., the degree of non-isoaxial alignment. With the determination of the differential value, the absolute reference sampler system 10 employs a stepper motor 58 for positioning the sampling head 22, and concurrently the collection inlet 24, that uses, or reacts, to the differential value to adjust the sampling head 22. The stepper motor 58 for positioning is operably connected to the sampling head 22, allowing the stepper motor 58 to turn, swivel or otherwise rotate the sampling head 22 into the wind direction 110 and fixing the collection inlet 24 in isoaxial alignment with the determined wind direction 110, i.e., the wind direction 110 data is used to control a stepper motor feedback system 58A (shown in FIG. 1) which swivels the sampling head 22.

Rotation of the sampling head 22 is achieved using a means for positioning 58 the sampling head 22, such as the stepper motor 58 in combination with the stepper motor feedback system 58A. Any suitable motor 58 may be used for moving the sampling head 22, with proper selection of the motor 58 being determinable by those skilled in the art in light of the disclosure herein. An example of such motor 58 includes a Hurst Model SAS4004-014 stepper motor controlled by a Hurst Model 220006 Stepper Motor Controller, manufactured by Hurst Manufacturing Division of Princeton, Ind., which is controlled by standard CMOS 5 volt logic level inputs. The stepper motor feedback system 58A preferably comprises a US Digital Corporation A2 absolute encoder attached to the shaft of the sampling head 22. The A2 encoder produces an analog voltage of 0 to 4.096 volts dc. These values represent the position or bearing of the collection inlet 24, with 0 Vdc representing 0 degrees, and 4.096 Vdc representing 359 degrees. All values between 0 Vdc and 4.096 Vdc are linearly related to the position of the collection inlet 24, i.e., 90 degrees is represented by 1.024 Vdc, 180 degrees is represented by 2.048 Vdc, 270 degrees is represented by 3.072 Vdc, etc. As further seen in FIG. 2 in the first comparison step of the comparator circuit 46, the representative voltage of the collection inlet 24 (shaft encoder) is compared electronically with the voltage from the wind direction sensor (wind direction), such as a Fidelity Model 500 wind direction sensor, manufactured by Cossonay Meteorology Systems of Reading, Pa. The voltage for the wind direction sensor has the same characteristics as that of the shaft encoder, with 0 Vdc representing 0 degrees, 1.024 Vdc representing 90 degrees, 2.048 Vdc representing 180 degrees, 3.072 Vdc representing 270 degrees, 4.096 Vdc representing 359 degrees, and all interposed values corresponding linearly. When the wind direction voltage is greater than that of the shaft encoder voltage, the stepper motor 58 (shown in FIG. 1) is directed to turn clockwise until the difference between the two voltages is minimal, at which time the stepper motor 58 is disabled until the wind direction changes again. When the wind direction voltage is smaller than that of the shaft encoder voltage, the stepper motor 58 is directed to turn counter-clockwise until the difference between the two voltage values becomes minimal, at which time the stepper motor 58 is disabled until the wind direction changes again.

Problematic with the comparator circuit 46, large excursions of the sampler head 22 may occur when attempting to cross from 359 degrees to 1 degree, or any time it is required to cross 0 degree. This problem is alleviated by computing the difference voltage between the wind direction sensor and the shaft encoder sensor. For occasions when the shaft position crosses 0 degrees, which would result in large 300+ degree excursions of the sampling head 22, an absolute magnitude of the difference between the wind direction voltage and shaft encoder voltage is computed. As such, when the difference is smaller than 2.048 Vdc (180 degrees), the stepper motor 58 reacts in the direction as previously described. An absolute magnitude of the voltage difference that exceeds half of the full scale voltage (2.048 Vdc) indicates that the sampling head 22 and the wind direction 110 are more than 180 apart, and that it would be shorter for the sampling head 22 to turn in the opposite direction. Accordingly, when the voltage difference is greater than 2.048 Vdc, the stepper motor 58 is instructed to turn in the opposite direction of the initial comparison, until the difference between the two voltages is minimal, at which time the stepper motor 58 is disabled. For example, when the wind direction 110 is at 10 degrees and the sampler head 22 is at 350 degrees (a difference of 340 degrees, and being greater than 180 degrees ), the sampler head 22 moves 20 degrees clockwise instead of 340 degrees counter-clockwise to realign to collection inlet 24 in isoaxial alignment with the wind direction 110.

Referring further to FIG. 2, the proper direction of turn for the sampling head 22 is accomplished at the second comparator, whose output is Exclusive-Ored (X-OR) with the output of the first comparator. If the output of the second comparator is logic level 1, the output of the X-OR gate will be the inverse of the input from the first comparator, therefore instructing the stepper motor 58 to turn in the opposite direction. The stepper motor 58 continues turning until the voltage difference falls below a threshold voltage set at the third comparator. When this occurs, the output of the third comparator goes to a high logic level and disables the stepper motor 58, as the sample head 22 becomes essentially in alignment with the wind direction 110. Once disabled, the stepper motor 58 remains disabled until the difference voltage exceeds the threshold voltage due to a change in wind direction 110.

Figure 3:
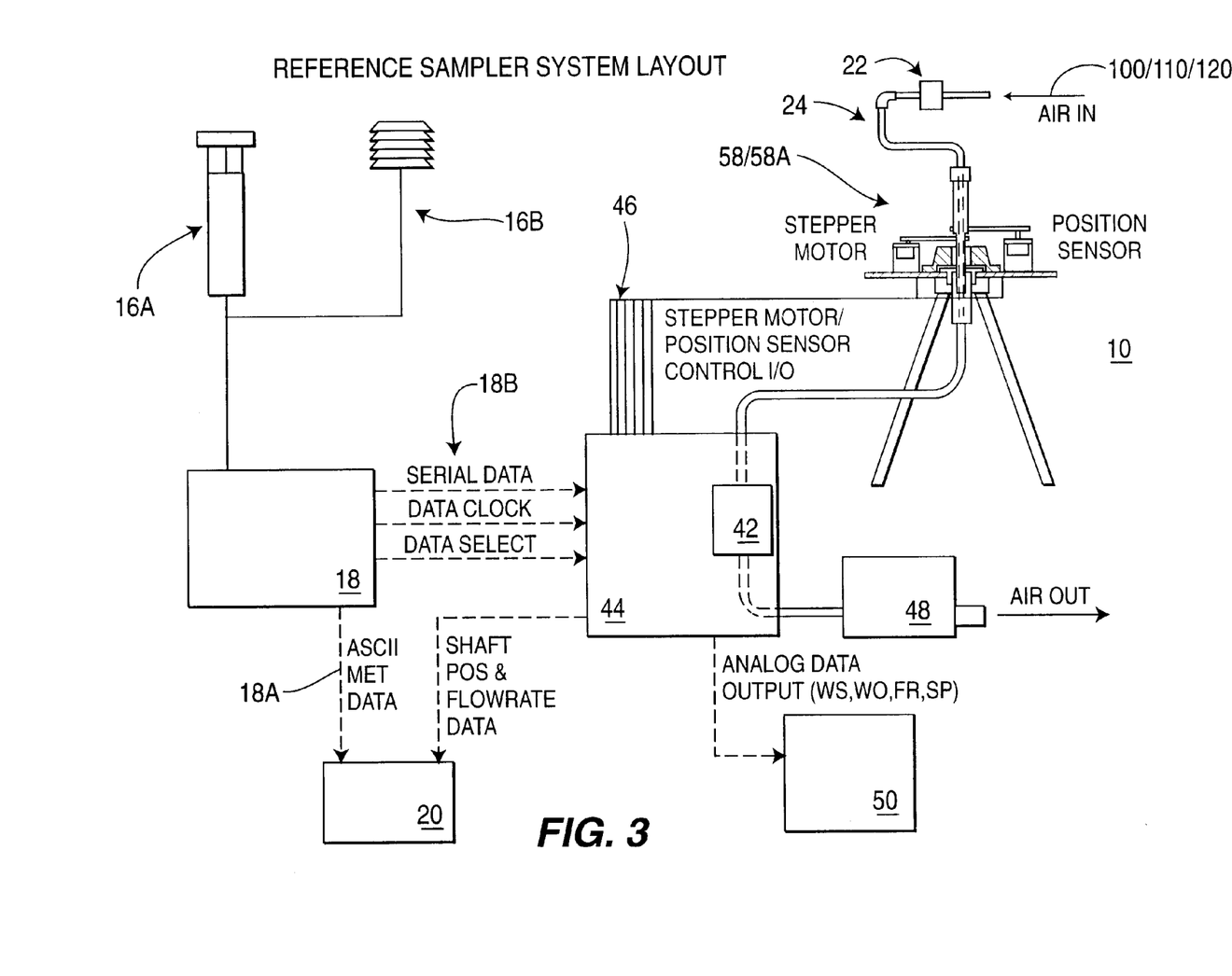
FIG. 3 is an operational schematic representation of the absolute reference sampler of the present invention.
Figure 4:
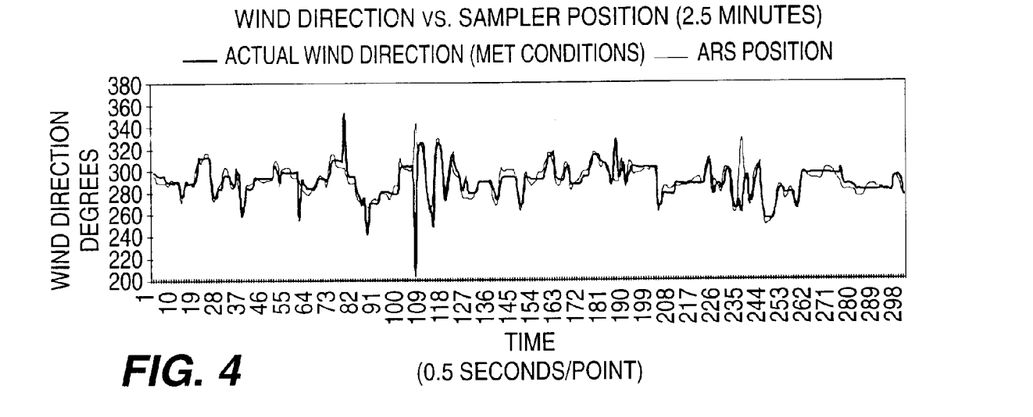
FIG. 4 is graphical representation of the wind direction compared to the collection inlet position of the present invention over time; and, FIG. 5 is graphical representation of the wind speed compared to the inlet speed of the present invention over time.
Figure 5:
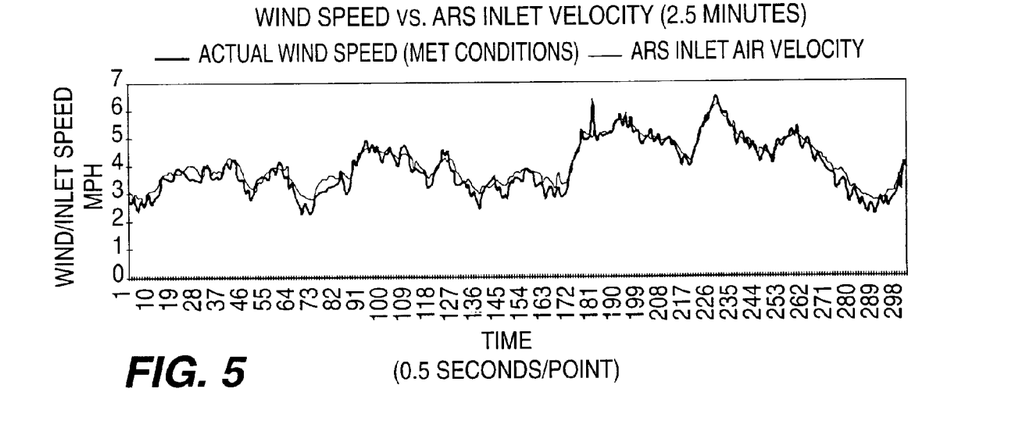

FIG. 3 is an operational schematic representation of the absolute reference sampler system 10. In a preferred embodiment as seen in FIG. 3, meteorological data is accumulated in real time by the Fidelity MET Sensor 16A and Fidelity Relative Humidity Sensor 16B. The information collected includes wind speed 120, wind direction 110, relative humidity, barometric pressure, and temperature. This information passes to the Fidelity Junction Box 18 through electrical cabling in the form of binary data. The data is processed in the Junction Box 18, where corrections are made to the wind speed data based on the current temperature, relative humidity, and barometric pressure. Four output signals originate from the Junction Box 18. One includes an ASCII formatted serial data stream 18A sent to an ASCII data logger 20 manufactured by Acumen Instruments of Ames, Iowa, which stores the data relating to wind speed 120, wind direction 110, relative humidity, and barometric pressure and temperature. ASCII comprises a standard format used for transmitting binary data between digital systems, preferably through RS-232 or RS-422 links. The data logger 20 stores the ASCII data for the length of the test, and can be analyzed later with a personal computer to determine whether the absolute reference sampler system 10 is properly functioning. The other three signals 18B from the junction box 18 pass to an electronic control box 44 through electrical cabling, and include three control signals: a serial data signal, data clock signal, and data select signal. These signals 18B are processed by the control box 44 to control the position of the sampling head 22. The feedback circuit, i.e., comparator circuit 46 (shown in FIG. 2) compares the wind direction 110 of the ambient air 100 information with the sampler head 22 position, and generates the appropriate control signals to the stepper motor 58 which turns the collection inlet 24 to the correct isoaxial position with the wind direction 110. These signals also contain the wind speed 120 information used to determine the proper pump 48 rate. The pump 48 pulls at a constant rate of revolutions per minute (rpm), yielding a free air capacity of greater than 100 liters per minute (lpm), using a mass flow controller 42 internal to the control box 44 restricts the amount of air passing through the collection inlet 24 in proportion to the wind speed 120. A set of analog voltage outputs is sent from the control box 44 to an external computer 50 containing a data acquisition card. These outputs are dc voltages ranging from 0 to +5 Volts dc which vary according to the sensor input, and represent wind speed 120, wind direction 110, sampling head 22 position, and inlet flow rate. The computer 50 converts these signals to a real time graphical display, allowing the operator to monitor the absolute reference sampler system 10 performance in real time, with the computer 50 additionally logging the collected data for later analysis.

In operation, the absolute reference sampler system 10 samples ambient air 100 by drawing an effective amount of ambient air 100 into the collection inlet 24. This effective amount of ambient air 100 occurs with the differential value relative to the wind direction 110 and sampling head 22 position is calculated causing the means for positioning 58 the sampling head 22 to rotate the sampling head 22 proportionally to the differential value to a calculated sampling head 22 position, with the mass flow controller 42 regulating the ambient air 100 flow into the collection inlet 24 to a speed substantially equivalent to the determined wind speed 120, e.g., a fixed rate pump pulls continuously at a rate of greater than 100 liters per minute free air capacity, while a 50 standard liters per minute (standard liters per minute) mass flow controller 42 varies or limits the flow rate at the tip of the collection inlet 24 in accordance with the wind speed 120 data determined by the meteorological station 16. Once the aerosol sample is collected in the filter 32, the filter 32 is removed from the swiveling sampling head 22 and the aerosol sample therefrom is analyzed.

While modulation of ambient air 100 intake occurs, the sampling head 22 is rotated for isoaxial alignment of the collection inlet 24 with the determined wind direction 110. Isoaxial alignment includes those angles that minimize or eliminate bias of a collected sample, as determinable by those skilled in the art in light of the disclosure here. Preferably isoaxial alignment ranges from equal to or less than about −3° to about +3°. Most preferably, the isoaxial alignment of the collection inlet 24 to the determined wind direction 110 is approximately 0°, with an unavoidable but minimal real time lag for positioning.

The absolute reference sampler 10 achieves proper directional alignment in real time through the use of the swiveling sampling head 22, and proper real time system flow rate through the use of a mass flow controller 42.

EXAMPLE 1

An absolute reference sampler prototype was built and tested. The absolute reference sampler was constructed using a mass flow controller transducer manufactured by Matheson Gas Products of Montgomeryville, Pa., an A2 Absolute Encoder with a shaft angle within a 360 degree range manufactured by US Digital Corporation of Vancouver, Wash., a Hurst Stepping Motor Controller, Model 220006, manufactured by Hurst of Princeton, Ind., and a meteorological sensing device of an Anemometer and Meteorological Sensor, Model 500CM-6 manufactured by Cossonay Meteorology Systems of Reading, Pa. for measuring wind speed and direction, temperature, pressure, and relative humidity. Critical parameters, such as wind speed, wind direction, flow rate and sampling head position were monitored in real time through use of a portable computer and data acquisition card. These parameters were logged to the computer's hard drive for analysis and archival purposes using Microsoft Excel. The prototype was portable, measuring 4.5 feet in height, 18 inches in depth and 12 inches in width, with a weight of 25 pounds.

Results of the tests are shown in FIGS. 4 and 5. As seen in the graph depicted in FIG. 4, the actual recorded wind direction is compared to the collection inlet position of the system of the present invention over a time period of 2.5 minutes. The alignment between the actual wind direction and sampler head has a maximum deviation of less than 100 degrees for less than 2 seconds (occurring at time about 109 seconds) with an overall mean deviation of approximately 5.9 degrees. For the hundreds of corrections evidenced within the time period of 2.5 minutes, the maximum deviation occurred when the present invention corrected in the opposite direction of the wind direction change, followed by an immediate recovery to the correct alignment. FIG. 5 is a graphic representation of the wind speed compared to the inlet speed of the present invention over time. The plot of FIG. 5 shows the system flow rate of the present invention matches the actual wind speed in real time over the test period of 2.5 minutes with close alignment. The correlation between the actual wind speed and the inlet air velocity has a maximum deviation of less than three standard liters per minute (slpm) (occurring at time about 1.5 minutes) with an overall mean deviation of approximately 0.23 slpm. With these preliminary data points of the performance of the actual sampling accuracy of the absolute reference sampler, the close correlation of sampler head position and system flow rate with the ambient wind conditions permit the absolute reference sampler to accurately collect ambient aerosol samples from a given environment in an unbiased manner.

EXAMPLE 2

(Flow Rate)

Prophetic

An absolute reference sampler of the present invention is constructed with fixed rate pump having a continuous pull rate of greater than 100 liters per minute free air capacity. Within the sampler, a 50 standard liters per minute (standard liters per minute) mass flow controller varies the flow rate at the sampler tip to match the wind speed data, in real time, collected from an attached meteorological station. The mass flow controller proportions the valve to proportion air 100 flow through it in response to an electrical input of a 0–5 volt command voltage. An operational amplifier circuit computes the 0 to 5 Vdc command voltage based on the wind speed data. A 0 volt input produces a flow of 0 liters per minute and a 5 volt input produces a flow of 50 liters per minute, with input values between 0 and 5 corresponding in a linear manner (giving a proportion of the control voltage to the desired flow rate into the absolute reference sampler as a ratio of approximately 1:10). For example, a wind speed of 10 mph provides a flow rate of 34 (10×3.4) liters per minute from a Matheson command voltage of 3.4 (34/10) volts. The required flow rate for the mass flow controller is determined in the unshrouded probe configuration by the formula Flow rate=$(\pi/4)(\text{Diameter}_{inlet})^2\times$Wind Speed, where flowrate and wind speed are referenced to standard temperature (20° C.) and standard pressure (1 atmosphere). With an absolute reference sampler having an inlet with a diameter of 0.50 inches, the mass flow controller restricts the flow rate as seen below in Table 1:

TABLE 1

| wind speed | 0 mph | 5 mph | 7.35 mph | 10 mph | 14.7 mph | 22.05 mph | 29.4 mph |
|---|---|---|---|---|---|---|---|
| flow rate | 0 lpm | 17 lpm | 25 lpm | 34 lpm | 50 lpm | 75 lpm | 100 lpm |

As seen in Table 1, a wind speed of 7.35 miles per hour (mph) requires a flow rate of 25 liters per minute (lpm), a wind speed of 14.7 mph requires a flow rate of 50 lpm, a wind speed of 22.05 mph requires a flow rate of 75 lpm, and a wind speed of 29.4 mph requires a flow rate of 100 lpm. In the configuration within this Example 2, the maximum wind speed that can be accurately sampled without a shroud is 14.7 mph, as the mass flow controller can only handle a maximum of 50 liters per minute flow rate. A flow controller with a higher upper limit allows for accurate sampling at higher wind speeds.

The process of the present invention collects an unbiased aerosol sample from a given environment. As such, the present invention minimizes, or eliminates, the size distribution biases commonly introduced by currently available samplers.

The foregoing summary, description, examples and drawings of the invention are not intended to be limiting, but are only exemplary of the inventive features which are defined in the claims.

What is claimed is:

1. An absolute reference aerosol sampler system, comprising:
   (a) a positioning component, comprising:
      a sampling head having a collection inlet;
      means for determining wind direction, wherein said wind direction is determined in real time,
      means for comparing the position of said collection inlet and said determined wind direction, wherein a differential value is created; and,
      means for positioning said sampling head reactive to said differential value and operably connected to said sampling head, wherein said means for positioning said sampling head rotates said sampling head for isoaxial alignment with said determined wind direction; and,
   (b) an air intake component, comprising:
      a mass flow controller;
      means for determining wind speed, wherein said wind speed is determined in real time; and,
      means for drawing an effective amount of ambient air into said collection inlet, wherein said mass flow controller receives an input for said determined wind speed causing said mass flow controller to regulate ambient air flow into said collection inlet to a speed substantially equivalent to said determined wind speed; and
   wherein said absolute reference sampler system further comprises a sealed bearing system, wherein the air flow from said sampling head remains sealed to said means for drawing ambient air into said collection inlet.

2. The absolute reference aerosol sampler system of claim 1, further comprising a filter element contained within said sampling head for collecting aerosol samples from the ambient air entering said collection inlet.

3. The absolute reference sampler system of claim 1, wherein said sampling head comprises a swiveling sampling head.

4. The absolute reference sampler system of claim 1, further comprising a shroud attached to and surrounding said collection inlet.

5. The absolute reference sampler system of claim 4, wherein the regulated ambient air flow into said collection inlet is represented by the equation: Flowrate=$x\pi$(Diameter$_{Shroud}$)$^2$×(Wind Speed)/4, wherein x is a variable determined by the ratio of the inlet diameter to the shroud diameter which is between 0 and 1 and equal to 1 when the shroud is absent.

6. The absolute reference sampler system of claim 1, wherein said means for determining real time wind direction comprises a portable meteorological station.

7. The absolute reference sampler system of claim 1, wherein said means for comparing the position of said collection inlet and said determined wind direction comprises a comparator circuit.

8. The absolute reference sampler system of claim 1, wherein said means for positioning said sampling head comprises a stepper motor feedback system.

9. The absolute reference sampler system of claim 1, wherein said mass flow controller comprises a proportioning valve and flowmeter.

10. The absolute reference sampler system of claim 1, wherein said mass flow controller regulates the amount of ambient air drawn into said collection inlet to an amount determined by Drawn Ambient Air=$(\pi/4)$(Diameter$_{inlet}$)$^2$×(Wind Speed) for an unshrouded inlet.

11. The absolute reference sampler system of claim 1, wherein said means for determining wind speed comprises a portable meteorological station.

12. The absolute reference sampler system of claim 1, wherein said means for drawing ambient air into said collection inlet comprises a pump.

13. The absolute reference sampler system of claim 1, wherein said system is portable.

14. A method for ambient aerosol sampling, comprising the steps of:
   (a) providing an absolute reference sampler system, comprising:
      a positioning component, comprising:
         a sampling head having a collection inlet and a filter element;
         means for determining wind direction, wherein said wind direction is determined in real time;
         means for comparing the position of said collection inlet and said determined wind direction, wherein a differential value is created; and,
         means for positioning said sampling head reactive to said differential value and operably connected to said sampling head, wherein said means for positioning said sampling head rotates said sampling head for isoaxial alignment with said determined wind direction, and,
      an air intake component, comprising:
         a mass flow controller;
         means for determining wind speed, wherein said wind speed is determined in real time; and,
         means for drawing an effective amount of ambient air into said collection inlet, wherein said mass flow controller receives an input for said determined wind speed causing said mass flow controller to regulate ambient air flow into said collection inlet to a speed substantially equivalent to said determined wind speed; and,
   wherein said absolute reference sampler system further comprises a sealed hearing system, wherein the air flow from said sampling head remains sealed to said means for drawing ambient air into said collection inlet; and
   (b) drawing an effective amount of said ambient air into said collection inlet,
   wherein said differential value relative to said wind direction and sampling head position is calculated causing said means for positioning said sampling head to rotate said sampling head proportionally to said differential value to a calculated position; and,
   wherein said mass flow controller regulates the ambient air flow into said collection inlet to a speed substantially equivalent to said determined wind speed.

15. The method of claim 14, further comprising the steps of:
   removing said filter from said swiveling sampling head; and,
   analyzing the aerosols collected therein.

16. The method of claim 14, wherein said means for drawing ambient air into said collection inlet comprises a pump of sufficient capacity to overcome pressure drop across said mass flow controller while maintaining an air speed at said collection inlet equivalent to ambient wind speed.

17. The method of claim 14, wherein said mass flow controller reduces the flow rate to an amount of: Drawn Ambient Air=$x\pi(\text{Diameter}_{Shroud})^2 \times (\text{Wind Speed})/4$, wherein x is a variable related to the ratio of the inlet diameter to the shroud diameter which is between 0 and 1 and equal to 1when the shroud is absent.

18. The method of claim 14, wherein said means for positioning said sampling head rotates said sampling head for isoaxial alignment of said collection inlet and said determined wind direction within a range from about −3° to about +3°.

19. The method of claim 18, wherein the isoaxial alignment of said sampling head and said determined wind direction is approximately 0°.

\* \* \* \* \*